United States Patent [19]

Tone et al.

[11] Patent Number: 4,755,513
[45] Date of Patent: Jul. 5, 1988

[54] ANTIMICROBIAL 1-SUBSTITUTED PHENYL-4-OXOQUINOLINE-3-CARBOXYLIC ACID COMPOUNDS

[75] Inventors: Hitoshi Tone; Hisashi Miyamoto; Hiraki Ueda; Kazuyuki Nakagawa, all of Tokushima, Japan

[73] Assignee: Otsuka Pharmaceutical Company, Limited, Tokyo, Japan

[21] Appl. No.: 766,337

[22] Filed: Aug. 16, 1985

[30] Foreign Application Priority Data

Jan. 30, 1985 [JP] Japan .................. 60-17256
Jul. 19, 1985 [JP] Japan ................. 60-160808
Jul. 19, 1985 [JP] Japan ................. 60-160809

[51] Int. Cl.$^4$ ................ A61K 31/495; C07D 401/04
[52] U.S. Cl. .......................... 514/254; 544/363
[58] Field of Search .................... 544/363; 514/254

[56] References Cited

U.S. PATENT DOCUMENTS

| 4,398,029 | 8/1983 | Irikura et al. | 544/363 |
| 4,429,127 | 1/1984 | Irikura et al. | 544/363 |
| 4,448,962 | 5/1984 | Irikura et al. | 544/363 |
| 4,528,287 | 7/1985 | Itoh et al. | 544/363 |

FOREIGN PATENT DOCUMENTS

| 0131839 | 1/1985 | European Pat. Off. . |
| 0154780 | 9/1985 | European Pat. Off. . |
| 2391210 | 12/1978 | France . |
| 2424919 | 11/1979 | France . |
| 2437406 | 4/1980 | France . |
| 1147336 | 4/1969 | United Kingdom . |

OTHER PUBLICATIONS

Chu, "Chemical Abstracts", vol. 103, 1985, col. 103:123373b.

Primary Examiner—Glennon H. Hollrah
Assistant Examiner—James H. Turnipseed
Attorney, Agent, or Firm—Wegner & Bretschneider

[57] ABSTRACT

Novel 1-substituted phenyl-4-oxoquinoline-3-carboxylic acid compounds of the formula:

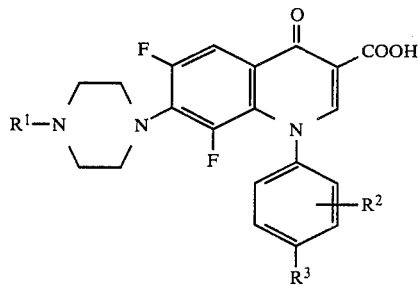

wherein $R^1$ is hydrogen atom or an alkyl having 1 to 2 carbon atoms, $R^2$ is hydrogen atom or fluorine atom, and $R^3$ is hydroxy, fluorine atom or an alkanoyloxy having 1 to 6 carbon atoms, and a pharmaceutically acceptable salt thereof, said compounds having excellent antimicrobial activity and hence being useful as an antimicrobial agent, and a pharmaceutical composition comprising as an active ingredient said 1-substituted phenyl-4-oxoquinoline-3-carboxylic acid compounds or a pharmaceutically acceptable salt thereof in admixture with a pharmaceutically acceptable diluent or carrier.

4 Claims, No Drawings

ANTIMICROBIAL 1-SUBSTITUTED PHENYL-4-OXOQUINOLINE-3-CARBOXYLIC ACID COMPOUNDS

The present invention relates to novel antimicrobial benzoheterocyclic compounds and salts thereof, more particularly 1-substituted phenyl-4-oxoquinoline-3-carboxylic acid compounds of the formula:

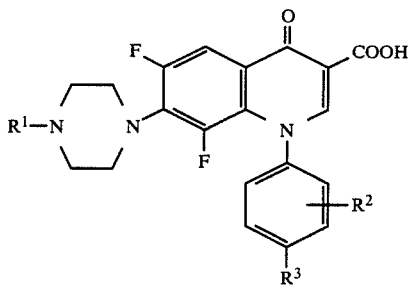

[1]

wherein $R^1$ is hydrogen atom or an alkyl having 1 to 2 carbon atoms, $R^2$ is hydrogen atom or fluorine atom, $R^3$ is hydroxy, fluorine atom or an alkanoyloxy having 1 to 6 carbon atoms, and pharmaceutically acceptable salts thereof.

The benzoheterocyclic compounds of the formula [1] and salts thereof have excellent antibacterial activities against various gram positive and gram negative bacteria, and are useful for the treatment of various infectious diseases induced by various bacteria in human, other animals and fish and are also useful as an external antimicrobial or disinfectant agent for medical instruments or the like.

PRIOR ART

The following compounds have been published in Interscience Conference Antimicrobial Agents and Chemotherapy held on October 8-10, 1984 (cf. Abstracts of The 984 ICAAC, page 102, Item 72).

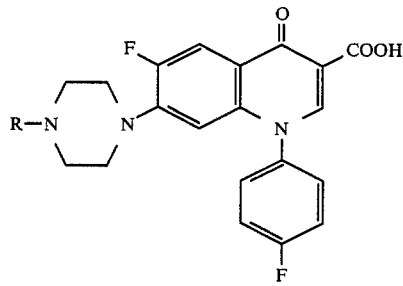

wherein R is hydrogen or methyl.

European Patent Publication No. 0131839 discloses the following compounds:

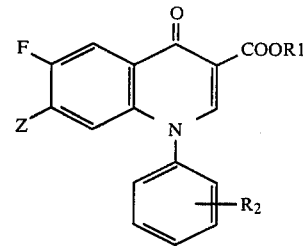

wherein $R_1$ is hydrogen or a carboxy protecting group, $R_2$ is hydrogen, halogen, nitro, carboxyl, cyano, methylenedioxy, an alkyl, a group of the formula: $-Y-R_3$ (Y is O or S, $R_3$ is hydrogen or an alkyl), an amine, and Z is an aliphatic heterocyclic ring including piperazine.

These known compounds are distinguished from the compounds [1] of the present invention in that no alkanoyloxy group is substituted on the phenyl ring at 1-position of the benzoheterocyclic nucleus and further in that no fluorine substituent is contained at 8-position. Besides, the compounds of the present invention show superior antimicrobial activity to the above known compounds as is clear from comparative experiments disclosed hereinafter.

BRIEF DESCRIPTION OF THE INVENTION

The object of the present invention is to provide novel benzoheterocyclic compounds of the formula [1] and salts thereof which have excellent antimicrobial activity and excellent absorbability. Another object of the invention is to provide a pharmaceutical composition containing as an active ingredient a compound of the formula [1] or a pharmaceutically acceptable salt thereof, which is useful for the treatment of various infectious diseases. These and other objects of the invention will be apparent to persons skilled in the art from the following description.

DETAILED DESCRIPTION OF THE INVENTION

The novel benzoheterocyclic compounds of the present invention have the formula [1] as mentioned above and include pharmaceutically acceptable salts thereof.

In the formula [1], the term "alkyl having 1 to 2 carbon atoms" for $R^1$ includes methyl and ethyl, preferably methyl. The term "alkanoyloxy having 1 to 6 carbon atoms" for $R^3$ includes formyloxy, acetyloxy, propionyloxy, butyryloxy, isobutyryloxy, pentanoyloxy, hexanoyloxy, etc., preferably an alkanoyloxy having 2 to 4 carbon atoms such as acetyloxy, propionyloxy, butyryloxy and isobutyryloxy, more preferably acetyloxy.

The groups $R^2$ and $R^3$ are preferably substituted at the positions as shown in the formula:

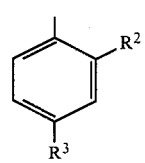

The group of the formula:

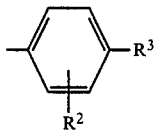

includes specifically 4-fluorophenyl, 2,4-difluorophenyl, 3,4-difluorophenyl, 4-hydroxyphenyl, 4-acetyloxyphenyl, 4-propionyloxyphenyl, 4-hexanoyloxyphenyl, 4-hydroxy-2-fluorophenyl, 4-hydroxy-3-fluoropheny, 4-acetyloxy-2-fluorophenyl, 4-acetyloxy-3-fluorophenyl, and the like. Preferred $R^2$ is hydrogen atom, and preferred $R^3$ is hydroxy and an alkanoyloxy group.

The compounds [1] and their salts of the present invention can be prepared by various processes, for example, by the process as shown in the following reaction schemes-I to -IV.

[Reaction scheme-I]

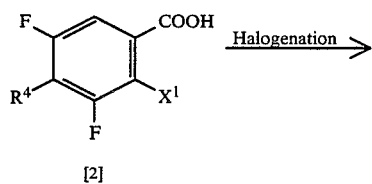

[2]

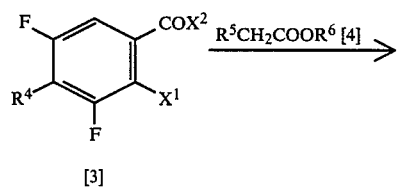

[3]

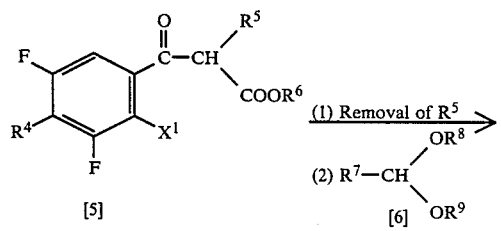

[5]

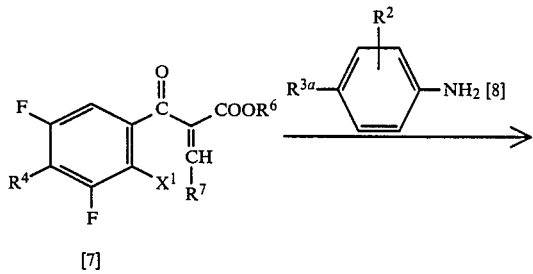

[7]

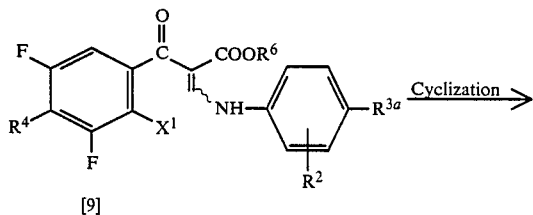

[9]

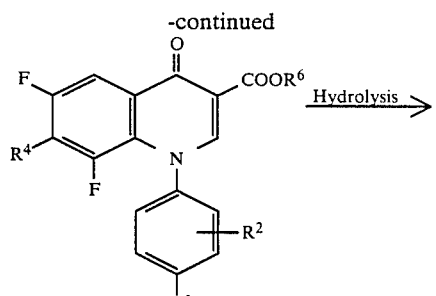

[10]

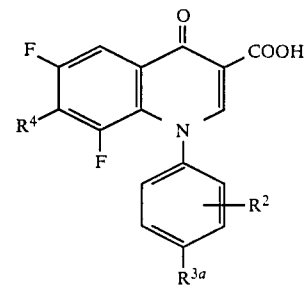

[11]

wherein $R^2$ is as defined above, $R^{3a}$ is hydroxy, an alkoxy having 1 to 6 carbon atoms or fluorine atom, $R^4$ is halogen atom or a group of the formula:

($R^1$ is as defined above), $R^5$ is a group of the formula: $-COR^{10}$ (wherein $R^{10}$ is an alkyl having 1 to 6 carbon atoms) or a group of the formula: $-COOR^{11}$ (wherein $R^{11}$ is an alkyl having 1 to 6 carbon atoms), $R^6$ is an alkyl having 1 to 6 carbon atoms, $R^7$ is a group of the formula:

(wherein $R^{12}$ and $R^{13}$ are each an alkyl having 1 to 6 carbon atoms) or an alkoxy having 1 to 6 carbon atoms, and $X^1$ and $X^2$ are each a halogen atom.

The halogenation of the compound [2] is carried out by reacting with a halogenating agent in the presence or absence of a solvent. The solvent includes aromatic hydrocarbons (e.g. benzene, toluene, xylene, etc.), halogenated hydrocarbons (e.g. dichloromethane, chloroform, carbon tetrachloride, etc.), ethers (e.g. dioxane, tetrahydrofuran, diethyl ether, etc.), dimethylformamide (DMF), dimethylsulfoxide (DMSO), and the like. The halogenating agent may be any conventional halogenating agents which can convert hydroxy in carboxy group into a halogen atom, and includes, for example, thionyl chloride, phosphorus oxychloride, phosphorus oxybromide, phosphorus pentachloride, phosphorus pentabromide, and the like. The amounts of the compound [2] and the halogenating agent are not specified, but, in case of using no solvent, the halogenating agent is usually used in a large excess amount, and in case of using a solvent, the halogenating agent is usually used in an amount of at least 1 mole, preferably 2 to 4 moles, per 1 mole of the compound [2]. The reaction temperature and the reaction period of time are not specified, either, but the reaction is usually carried out at a temperature of from room temperature to 100° C. for 30 minutes to 6 hours.

The reaction of the compound [3] and the compound [4] is carried out in a suitable solvent in the presence of a basic compound. The solvent may be any conventional solvents unless they give any undesirable effect on the reaction, and includes, for example, water, ethers (e.g. diethyl ether, dioxane, tetrahydrofuran, monoglyme, diglyme, etc.), alcohols (e.g. methanol, ethanol, isopropanol, etc.), aromatic hydrocarbons (e.g. benzene, toluene, xylene, etc.), aliphatic hydrocarbons (e.g. n-hexane, heptane, cyclohexane, ligroin, etc.), amines (e.g. pyridine, N,N-dimethylaniline, etc.), halogenated hydrocarbons (e.g. chloroform, dichloromethane, carbon tetrachloride, etc.), aprotic polar solvents (e.g. DMF, DMSO, hexamethyl phosphoric triamide (HMPA), etc.), and a mixture of these solvents. The basic compound includes inorganic bases (e.g. metallic sodium, metallic potassium, metallic magnesium, sodium hydride, sodium amide, sodium hydroxide, potassium hydroxide, sodium carbonate, potassium carbonate, sodium hydrogen carbonate, etc.), metal alcoholates (e.g. sodium methylate, sodium ethylate, etc.), and organic bases (e.g. pyridine, piperidine, quinoline, triethylamine, N,N-dimethylaniline, etc.). The reaction is usually carried out at a temperature of from 0° to 150° C., preferably from room temperature to 120° C., for 0.5 to 15 hours. The compound [4] is usually used in an amount of at least 1 mole, preferably 1 to 2 moles, per 1 mole of the compound [3]. The basic compound is usually used in an amount of at least 1 mole, preferably 1 to 2 moles, per 1 mole of the compound [3].

The compound [5] wherein $R^5$ is the group: $-COR^{10}$ is subjected to the reaction for removal of the group: $-COR^{10}$ in a solvent in the presence of a basic compound. The solvent includes ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, etc.), aprotic polar solvents (e.g. DMF, DMSO, HMPA, etc.), and the like. The basic compound includes ammonia gas, aqueous ammonia, ammonium salts (e.g. ammonium chloride, etc.), primary or secondary amines (e.g. ethylamine, diethylamine, piperidine, etc.), and the like. The reaction is usually carried out at a temperature of from 0° to 150° C., preferably from room temperature to 100° C., for 1 to 20 hours.

The compound [5] wherein $R^5$ is a group: $-COOR^{11}$ is subjected to the reaction for removal of the group: $-COOR^{11}$ in an aqueous solution in the presence of an acid catalyst. The acid catalyst includes mineral acids (e.g. hydrochloric acid, sulfuric acid, etc.) and organic acids (e.g. p-toluenesulfonic acid, etc.). The reaction is usually carried out at a temperature of from 0° to 150° C., preferably from room temperature to 100° C., for 1 to 20 hours.

The reaction of the $R^5$ group-removed compound and the compound [6] is carried out in a suitable solvent. The solvent may be any solvents which are used in the above reaction for the removal of the $R^5$ group. The reaction is usually carried out at a temperature of from 0° to 150° C., preferably from 0° to 100° C., for 0.5 to 10 hours. The comound [6] is usually used in an equimolar to large excess amount, preferably 1 to 2 moles per 1 mole of the compound [5]. In case of using a compound [6] wherein $R^7$ is a lower alkoxy group, the reaction may also be carried out by using acid anhydrides (e.g. acetic anhydride) as a solvent as well as above-mentioned solvents at a temperature of from 0° to 200° C., preferably 0° to 170° C.

The reaction of the compound [7] and the compound [8] is carried out in a suitable solvent. The solvent may be any conventional solvents unless they give any undesirable effect on the reaction, and includes, for example, alcohols (e.g. methanol, ethanol, propanol), ethers (e.g. diethyl ether, dioxane, tetrahydrofuran, monoglyme, diglyme, etc.), aromatic hydrocarbons (e.g. benzene, toluene, xylene, etc.), aliphatic hydrocarbons (e.g. n-hexane, heptane, cyclohexane, ligroin, etc.), halogenated hydrocarbons (e.g. chloroform, methylene chloride, carbon tetrachloride, etc.), aprotic polar solvents (e.g. DMF, DMSO, HMPA, etc.), and the like. The reaction is usually carried out at a temperature of from 0° to 150° C., preferably from room temperature to 100° C., for 0.5 to 15 hours. The compound [8] is usually used in an amount of at least 1 mole, preferably 1 to 2 moles, per 1 mole of the compound [7].

The cyclization of the compound [9] is carried out in a suitable solvent in the presence of a basic compound. The solvent may be any conventional solvents unless they give any undesirable effect on the reaction, and includes, for example, ethers (e.g. diethyl ether, dioxane, tetrahydrofuran, monoglyme, diglyme, etc.), aliphatic hydrocarbons (e.g. n-hexane, heptane, ligroin, etc.), halogenated hydrocarbons (e.g. chloroform, methylene chloride, carbon tetrachloride, etc.), aprotic polar solvents (e.g. DMF, DMSO, HMPA, etc.), and the like. The basic compound includes inorganic bases (e.g. metallic sodium, metallic potassium, sodium hydride, sodium amide, sodium hydroxide, potassium hydroxide, etc.), metal alcoholates (e.g. sodium methylate, sodium ethylate, etc.), and organic bases (e.g. 1,8-diazobicyclo[5.4.0]undecene-7 (DBU), N-benzyltrimethylammonium hydroxide, tetrabutylammonium hydroxide, etc.). The reaction is usually carried out at a temperature of from 0° to 150° C., preferably from room temperature to 120° C., for 0.5 to 5 hours. The basic compound is usually used in an amount of at least 1 mole, preferably 1 to 2 moles, per 1 mole of the compound [9].

The hydrolysis of the compound [10] can be carried out under the conditions of conventional hydrolysis, for instance, in the presence of a basic compound (e.g. sodium hydroxide, potassium hydroxide, barium hydroxide, etc.), a mineral acid (e.g. sulfuric acid, hydrochloric acid, nitric acid, hydrobromic acid, etc.) or an organic acid (e.g. acetic acid, aromatic sulfonic acids, etc.) in a solvent such as water, alcohols (e.g. methanol, ethanol, isopropanol, etc.), ketones (e.g. acetone, methyl ethyl ketone, etc.), ethers (e.g. dioxane, ethylene glycol, etc.), acetic acid, or a mixture thereof. The reaction is usually carried out at a temperature of from room temperature to 200° C., preferably 50° to 150° C., for 0.5 to 6 hours. By the reaction, there is produced the compound [11].

[Reaction Scheme-II]

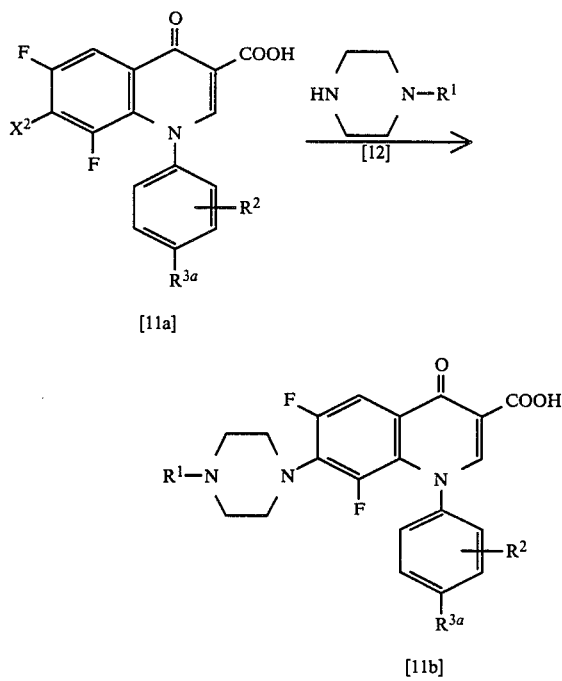

[11a]

[11b]

wherein $R^1$, $R^2$ and $R^{3a}$ are as defined above, and $X^2$ is a halogen atom.

The reaction of the compound [11a] and the compound [12] is carried out in a solvent, wherein both compounds are used in a wide range of ratio, and the compound [12] is usually used in an amount of at least 1 mole, preferably 1 to 5 moles, per 1 mole of the compound [11a]. The solvent includes water, alcohols (e.g. methanol, ethanol, isopropanol, butanol, amyl alcohol, isoamyl alcohol, etc.), aromatic hydrocarbons (e.g. benzene, toluene, xylene, etc.), ethers (e.g. tetrahydrofuran, dioxane, diglyme, etc.), DMF, DMSO, HMPA, N-methylpyrrolidone, or the like. Among these solvents, the preferred one is DMF, DMSO, HMPA, and N-methylpyrrolidone. The reaction may also be carried out in the presence of an acid-removing agent, such as inorganic carbonates (e.g. sodium carbonate, potassium carbonate, sodium hydrogen carbonate, potassium hydrogen carbonate, etc.) or tertiary amines (e.g. pyridine, quinoline, triethylamine, etc.). The reaction is usually carried out under a pressure of from 1 to 20 atm., preferably from 1 to 10 atm., at a temperature of from 100° to 250° C., for 1 to 20 hours.

The compound [11] or [11b] wherein $R^{3a}$ is an alkoxy having 1 to 6 carbon atoms can be converted into the corresponding compound wherein $R^3$ is hydroxy by treating it with an acid in a solvent or without using any solvent. The solvent includes water, aromatic hydrocarbons (e.g. nitrobenzene, toluene, benzene, etc.), saturated hydrocarbons (e.g. hexane, octane, etc.), lower alcohols (e.g. methanol, ethanol, isopropanol, etc.), ethers (e.g. dioxane, tetrahydrofuran, etc.), ketones (e.g. acetone, etc.), acetic acid, acetonitrile, and a mixture thereof. The acid includes mineral acids (e.g. hydrochloric acid, sulfuric acid, hydrobromic acid, etc.), carboxylic acids (e.g. p-toluenesulfonic acid, pyridine, p-toluenesulfonate, acetic acid, propionic acid, etc.), aluminum chloride, tin chloride, boron fluoride, zinc chloride, boron tribromide, boron trichloride, and the like. These acids may be used in an amount of at least equimolar to the starting compound, and usually in a large excess amount. The reaction is usually carried out at a temperature of from −30° to 200° C., preferably −30° to 150° C., for 0.5 to 8 hours.

The compound [10] in Reaction Scheme-I wherein $R^{3a}$ is an alkoxy having 1 to 6 carbon atoms can be converted into the correspond compound wherein $R^{3a}$ is hydroxy in the same manner as described above.

The compound [1] wherein $R^3$ is hydroxy can be converted into the corresponding compound wherein $R^3$ is an alkanoyloxy having 1 to 6 carbon atoms by treating it with an alkanoylation agent. The alkanoylation agent includes a compound of the formula: $(R^{14})_2O$ or $R^{14}X^3$ wherein $R^{14}$ is an alkanoyl having 1 to 6 carbon atoms and $X^3$ is a halogen atom. The reaction can be carried out in the presence or absence of a solvent. The solvent may be any conventional solvents unless they give any undesirable effect on the reaction, and includes, for example, halogenated hydrocarbons (e.g. dichloromethane, dichloroethane, chloroform, carbon tetrachloride), aromatic hydrocarbons (e.g. benzene, toluene, xylene), ethers (e.g. diethyl ether, tetrahydrofuran, dioxane), pyridine, and the like. The alkanoylation agent is used in an amount of at least equimolar to the starting compound, preferably in an excess amount. The reaction is usually carried out at a temperature of from 0° to 150° C., preferably from 0° to 100° C., for 1 to 24 hours. The above reaction may also be carried out in the presence of a tertiary amine (e.g. pyridine, triethylamine).

[Reaction Scheme-III]

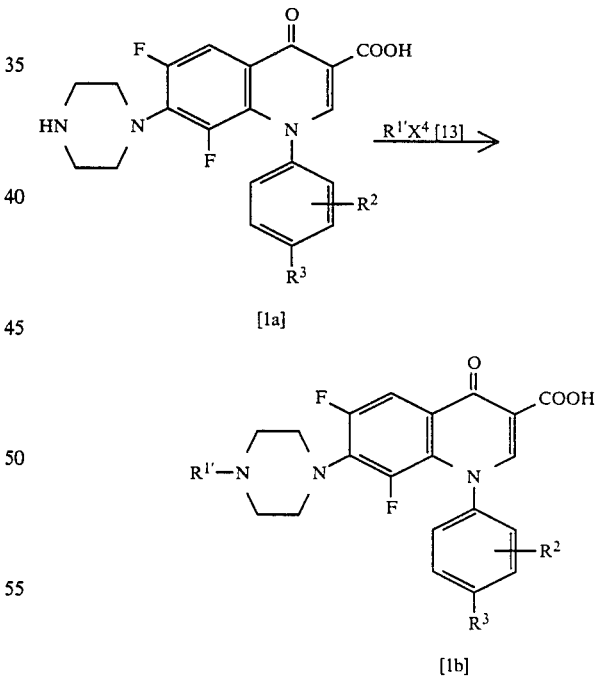

[1a]

[1b]

wherein $R^2$ and $R^3$ are as defined above, $R^{1'}$ is an alkyl having 1 to 2 carbon atoms, and $X^4$ is a halogen atom.

The reaction of the compound [1a] and the compound [13] is carried out in the presence of a hydrohalogenating agent in an appropriate solvent. The solvent includes water, alcohols (e.g. methanol, ethanol, isopropanol), ketones (e.g. acetone, methyl ethyl ketone), ethers (e.g. diethyl ether, dioxane), aromatic hydrocarbons (e.g. benzene, toluene, xylene, etc.), and the like. The dehydrohalogenating agent includes inorganic bases (e.g. sodium hydroxide, potassium hydroxide, sodium carbonate, potassium carbonate), alkali metals (e.g. sodium, potassium), and organic bases (e.g. pyridine, piperidine). The compound [13] is used in an amount of at least equimolar to the starting compound [1a] or in excess amount, preferably about 1 to 3 moles to 1 mole of the compound [1a]. The reaction is usually carried out at a temperature of from room temperature to 150° C., preferably at 50° to 120° C., for about 1 to 12 hours.

[Reaction Scheme-IV]

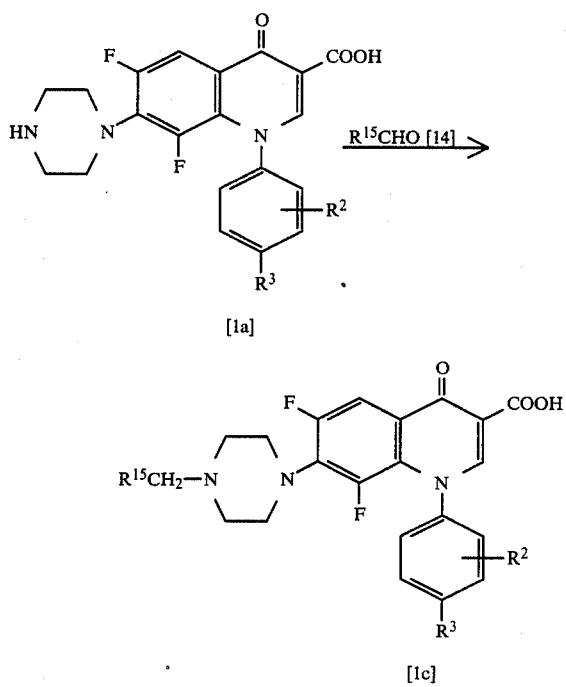

[1a]

[1c]

wherein $R^2$ and $R^3$ are as defined above, $R^{15}$ is hydrogen atom or methyl.

The reaction of the compound [1a] and the compound [14] is carried out in the presence of a reducing agent in an appropriate solvent or without using any solvent. The solvent includes for example, water, alcohols (e.g. methanol, ethanol, isopropanol), acetic acid, ethers (e.g. dioxane, diethyl ether, diglyme, tetrahydrofuran), aromatic hydrocarbons (e.g. benzene, toluene, xylene, etc.), and the like. The reducing agent includes formic acid, hydroxy reducing agents (e.g. sodium borohydroxide, sodium borocyanohydroxide, aluminum lithium hydroxide), catalytic reducing agents (e.g. palladium black, palladium carbon, platinum oxide, platinum black, Raney nickel) and the like. When formic acid is used as the reducing agent, the reaction is usually carried out at a temperature of from room temperature to 200° C., preferably at 50° to about 150° C., for about 1 to 10 hours. Formic acid is used in an amount of a large excess amount to the compound [1a]. When a hydroxy reducing agent is used, the reaction is usually carried out at a temperature of from −30° to 100° C., preferably at 0° to 70° C., for 30 minutes to 12 hours. The reducing agent is used in an amount of 1 to 20 moles, preferably 1 to 5 moles, per 1 mole of the compound [1a]. Particularly, when aluminum lithium hydroxide is used as the reducing agent, the solvent is preferably ethers (e.g. diethyl ether, dioxane, tetrahydrofuran, diglyme) and aromatic hydrocarbons (e.g. benzene, toluene, xylene). When a catalytic reducing agent is used, the reaction is usually carried out under a pressure of from atmospheric pressure to 20 atm., preferably from atmospheric pressure to 10 atm, at a temperature of from −30° to 100° C., preferably 0° to 60° C., for 1 to 12 hours. The catalyst is usually used in an amount of 0.1 to 40% by weight, preferably 1 to 20% by weight, based on the weight of the compound [1a]. The compound [14] is usually used in at least equimolar amount, preferably equimolar to a large excess amount, to the compound [1a].

The compounds [1] can easily be converted into a salt thereof by treating them with a pharmaceutically acceptable acid or base. The acid includes inorganic acids (e.g. hydrochloric acid, sulfuric acid, phosphoric acid, hydrobromic acid, etc.) and organic acids (e.g. succinic acid, maleic acid, fumaric acid, malic acid, tartaric acid, citric acid, benzoic acid, etc.). The base includes sodium hydroxide, potassium hydroxide, calcium hydroxide, sodium carboante, potasium hydrogen carbonate, and the like.

The compound thus obtained can easily be isolated by conventional methods, such as extraction with solvents, dilution method, recrystallization, column chromatography, preparative thin layer chromatography, and the like.

Among the compounds of the present invention, the compounds of the formula [1b] show particularly excellent antimicrobial activity against *Staphylococcus aureus, Staphylococcus pyrogenes,* Pseudomonas, anaerobe, various resistant strains of gram positive or negative bacteria, and hence, are useful as an antimicrobial agent for the treatment of diseases induced by these microorganisms. These compounds show also low toxicity and less side effect and are characteristic in good absobability and in sustained activity.

Among the preferred compounds [1b], particularly preferred compounds are the compounds of the formula [1b] wherein $R^{1'}$ is hydrogen or methyl, more preferably methyl, $R^2$ is hydrogen atom or fluorine atom, more preferably fluorine, and $R^3$ is hydroxy or an alkanoyloxy having 2 to 4 carbon atoms, more preferably acetyloxy.

The compounds of the present invention are usually used in the form of a usual pharmaceutical preparation. The pharmaceutical preparation can be prepared in admixture with conventional pharmaceutically acceptable diluents or carriers, such as fillers, weighting agents, binding agents, wetting agents, disintegrators, surfactants, rublicating agents, and the like. The pharmaceutical preparation includes various preparations suitable for treatment of the diseases, for example, tablets, pills, powders, solutions, suspensions, emulsions, granules, capsules, suppositories, injections (solutions, suspensions, etc.), and the like. In the preparation of tablets, there may be used any conventional carriers, for example, vehicles (e.g. lactose, white sugar, sodium chloride, glucose, urea, starches, calcium carbonate, kaolin, crystalline cellulose, silicate, etc.), binding agents (e.g. water, ethanol, propanol, simple syrup, glucose solution, starch solution, gelatin solution, carboxymethyl cellulose, shellac, methyl cellulose, potassium phosphate, polyvinylpyrrolidone, etc.), disintegrators (e.g. dry starch, sodium alginate, agar powder, laminaran powder, sodium hydrogen carbonate, calcium carbonate, polyoxyethylene sorbitan fatty acid esters, sodium laurylsulfate, stearic monoglyceride, starches, lactose, etc.), disintegration inhibitors (e.g. white sugar, stearin, cacao butter, hydrogenated oils, etc.), absorption promoters (e.g. quaternary ammonium salts, sodium laurylsulfate, etc.), wetting agents (e.g. glycerin, starches, etc.), adsorbents (e.g. starches, lactose, kaolin, bentonite, colloidal silicates, etc.), rublicants (e.g. purified talc, stearates, boric acid powder, polyethylene glycol, etc.), and the like. The tablets may also be coated with conventional coating agents, for example, may be in the form of a sugar coated tablet, a gelatin-coated tablets, an enteric coating tablet, a film coating tablet, or a double or multiple layers tablet. In the preparation of pills, there may be used conventional carries, such as vehicles (e.g. glucose, lactose, starches, cacao butter, hydrogenated vegetable oils, kaolin, talc, etc.), binding agents (e.g. gum arabic powder, tragacanth powder, gelatin, ethanol, etc.), disintegrators (e.g. laminaran, agar, etc.), and the like. In the preparation of suppositories, there may be used conventional carriers, such as polyethylene glycol, cacao butter, higher alcohols, higher alcohol esters, gelatin, semi-synthetized glycerides, and the like. In the preparation of injections, the solutions, emulsions or suspensions of the compounds are sterilized and are preferably made isotonic with the body liquid. These solutions, emulsions and suspensions are prepared by admixing the active compound with a conventional diluent, such as water, ethyl alcohol, propylene glycol, ethoxylated isostearyl alcohol, polyoxylated isostearyl alcohol, polyoxyethylene sorbitan fatty acid esters, and the like. The preparations may also be incorporated with sodium chloride, glucose or glycerin in an amount sufficient to make them isotonic with the body liquid. The preparations may also be incorporated with conventional solubilizers, buffering agents, anesthetizing agents, and further, with coloring agents, presevatives, perfumes, flavors, sweeting agents, and other medicaments. The preparations in the form of a paste, cream or gel may be prepared by using as a diluent white vaseline, paraffin, glycerin, cellulose derivatives, polyethylene glycol, silicone, bentonite, or the like.

The active compounds [1] or salts thereof may be contained in any amount in the preparations, and are usually contained in an amount of 1 to 70% by weight based on the whole weight of the preparations.

The pharmaceutical preparations of the present invention can be administered in any methods. Suitable method for administration may be selected in accordance with the preparation form, age and sex of the patients, degree of severity of the diseases, and the like. For instance, tablets, pills, solutions, suspensions, emulsions, granules and capsules are administered in oral route. In case of injection, it is administered intravenously alone or together with an auxiliary liquid (e.g. glucose, amino acid solution). The injections may also be administered in intramuscular, intracutaneous, subcutaneous, or intraperitoneal route. Suppositories are administered in intrarectal route.

The dosage of the pharmaceutical preparations of the present invention may vary according to administration methods, age and sex of the patients, severity of the diseases, and the like, but is usually in the range of about 0.2 to 100 mg of the active compound [1] or a salt thereof per 1 kg of body weight of the patient per day. The preparation is usually administered by dividing into 2 to 4 times per day.

The present invention is illustrated by the following Reference Examples, Examples, Preparations, and Experiments.

REFERENCE EXAMPLE 1

Magnesium ribbon (0.11 g) is suspended in absolute ethanol (0.5 ml), and thereto is added carbon tetrachloride (0.05 ml). After 10 minutes, to the mixture is added dropwise a mixture of diethyl malonate (1.5 ml), absolute ethanol (0.9 ml) and anhydrous ether (3.8 ml) at a room temperature. After the addition, the mixture is refluxed for 3 hours. Thereafter, a solution of 2,3,4,5-tetrafluorobenzoyl chloride (2.0 g) in anhydrous ether (0.9 ml) is added dropwise under ice-cooling. After the addition, the mixture is stirred at room temperature for 3 hours, and then allowed to stand overnight. A mixture of ice-water (4 ml) and conc. sulfuric acid (0.24 ml) is added dropwise to the reaction mixture under ice-cooling, and the mixture is stirred at room temperature for 30 minutes. The ether layer is separated, and the remaining reaction mixture is extracted with ether. The ether layers are combined, and are washed with saturated aqueous sodium chloride solution and dried over magnesium sulfate. The solvent is distilled off under reduced pressure to give diethyl 2,3,4,5-tetrafluorobenzoylmalonate (3.0 g).

Diethyl 2,3,4,5-tetrafluorobenzoylmalonate (2.9 g) and p-toluenesulfonic acid (15 mg) are added to water (5 ml), and the mixture is refluxed for 3 hours. After cooling, the reaction mixture is extracted with dichloromethane. The dichloromethane layer is washed with saturated aqueous sodium chloride solution and dried over magnesium sulfate. After distilling off the solvent under reduced pressure, the residue is purified by silica gel column chromatography (solvent, chloroform: n-hexane=1:1) to give ethyl α-(2,3,4,5-tetrafluorobenzoyl)acetate (0.8 g), m.p. 44.5°–45.5° C.

REFERENCE EXAMPLE 2

A mixture of ethyl α-(2,3,4,5-tetrafluorobenzoyl)acetate (0.7 g), ethyl orthoformate (0.67 g) and acetic anhydride (0.74 g) is heated at 150° C. for 1.5 hour. After the reaction, the volatile material is distilled off at 120° C. under reduced pressure with a water pump to give ethyl 2-(2,3,4,5-tetrafluorobenzoyl)-3-ethoxyacrylate (0.8 g) as a mixture of cis and trans isomers.

NMR (CDCl$_3$) δ: 7.70, 7.75 (s, 1H), 7.28–7.61 (m, 1H) 4.02–4.46 (m, 4H), 1.05–1.52 (m, 6H).

REFERENCE EXAMPLE 3

A mixture of ethyl 2-(2,3,4,5-tetrafluorobenzoyl)-3-ethoxyacrylate (0.4 g), p-anisidine (0.15 g) and ethanol (4 ml) is stirred at room temperature for 30 minutes. After the reaction, the solvent is distilled off under reduced pressure. To the residue is added anhydrous dioxane (10 ml) and thereto is further added portionwise 60% sodium hydride (60 mg). The mixture is stirred at room temperature for 30 minutes. The reaction mixture is poured into saturated aqueous ammonium chloride, and the mixture is extracted with dichloromethane to give ethyl 6,7,8-trifluoro-1-(4-methoxyphenyl)-1,4-dihydro-4-oxoquinoline-3-carboxylate (0.37 g).

REFERENCE EXAMPLE 4

A mixture of ethyl 6,7,8-trifluoro-1-(4-methoxyphenyl)-1,4-dihydro-4-oxoquinoline-3-carboxylate (0.37 g), conc. hydrochloric acid (1 ml) and 90% acetic acid (4 ml) is heated at 120° C. for 1 hour. After cooling, the precipitated crystals are separated by filtration, washed with water and with a mixture of ethanol and ether to give 6,7,8-trifluoro-1-(4-methoxyphenyl)-1,4-dihydro-4-oxoquinoline-3-carboxylic acid (0.3 g).

Elementary analysis for $C_{17}H_{10}NO_4F_3$: Calcd. (%): C, 58.46; H, 2.89; N, 4.01. Found (%): C, 58.43; H, 2.81, N, 4.11.

M.p. 252°–254° C., white crystals.

REFERENCE EXAMPLE 5

A mixture of ethyl 6,7,8-trifluoro-1-(4-methoxyphenyl)-1,4-dihydro-4-oxoquinoline-3-carboxylate (0.37 g) and 47% hydrobromic acid (4 ml) is heated at 120° C. for 3 hour. After cooling, the precipitated crystals are separated by filtration, washed with water and with a mixture of ethanol and ether to give 6,7,8-trifluoro-1-(4-hydroxyphenyl)-1,4-dihydro-4-oxoquinoline-3-carboxylic acid (0.26 g).

Elementary analysis for $C_{16}H_8NO_4F_3$: Calcd. (%): C, 57.33; H, 2.41; N, 4.18. Found (%): C, 57.28; H, 2.47, N, 4.11.

M.p. >300° C., white crystals.

NMR (trifluoroacetic acid) δ: 9.33 (s, 1H), 8.46 (dt, 1H, J=10 Hz, 7.5 Hz, 2.5 Hz) 7.56 (d, 2H, J=9 Hz), 7.27 (d, 2H, J=9 Hz).

REFERENCE EXAMPLES 6–7

In the same manner as described in Reference Example 4 by using appropriated starting materials, the following compounds are obtained.

6,7,8-Trifluoro-1-(4-fluorophenyl)-1,4-dihydro-4-oxoquinoline-3-carboxylic acid, m.p. 263°–266° C., colorless crystals.

6,7,8-Trifluoro-1-(2-fluoro-4-hydroxyphenyl)-1,4-dihydro-4-oxoquinoline-3-carboxylic acid, m.p. >300° C., colorless crystals, NMR (trifluoroacetic acid) δ: 9.31 (1H, s), 8.45 (1H, ddd, J=10 Hz, 7.5 Hz, 2.5 Hz), 7.60 (1H, t, J=7.5 Hz), 7.06 (2H, dd, J=7.5 Hz, 2 Hz).

EXAMPLE 1

6,7,8-Trifluoro-1-(4-hydroxyphenyl)-1,4-dihydro-4-oxoquinoline-3-carboxylic acid (0.10 g) is suspended in N-methylpyrrolidone (2 ml), and thereto is added N-methylpiperazine (0.15 g), and the mixture is stirred at 90° C. for 30 minutes. After completion of the reaction, the solvent is distilled off under reduced pressure, and the residue is washed with ethanol and recrystallized from DMF to give 6,8-difluoro-1-(4-hydroxyphenyl)-7-(4-methyl-1-piperazinyl)-1,4-dihydro-4-oxoquinoline-3-carboxylic acid (0.08 g) as pale yellowish white crylstals, m.p. >300° C.

Elementary analysis for $C_{21}H_{19}NO_3O_4F_2$: Calcd. (%): C, 60.72; H, 4.61; N, 10.12. Found (%): C, 60.64; H, 4.53; N, 10.18.

NMR (trifluoroacetic acid) δ: 9.18 (s, 1H), 8.30 (dd, 1H, J=12 Hz, 2.5 Hz), 7.51 (d, 2H, J=9 Hz), 7.25 (d, 2H, J=9 Hz), 3.27 (m, 8H), 3.15 (d, 3H, J=5 Hz)

EXAMPLES 2–6

In the same manner as described in Example 1, the compounds as shown in Table 1 are prepared.

TABLE 1

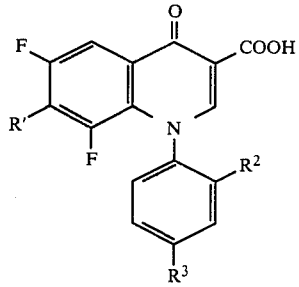

| Ex. No. | R' | $R^2$ | $R^3$ | Crystalline form (Recrystalliz. solvent) | m.p. (°C.) |
|---|---|---|---|---|---|
| 2 | —N⟨ ⟩NH | H | OH | Pale yellowish white crystals (DMF) | >300* |
| 3 | —N⟨ ⟩NH | H | F | Pale yellowish white crystals (DMF) | 281–283 |
| 4 | —N⟨ ⟩N—CH₃ | H | F | Pale yellowish white crystals (Ethanol) | 278–280 |
| 5 | —N⟨ ⟩NH | F | OH | Pale yellowish white crystals (DMF) | 293–297 (dec.) |
| 6 | —N⟨ ⟩N—CH₃ | F | OH | Pale yellowish white crystals (DMF-ethanol) | 298–303 (dec.) |

*NMR (trifluoroacetic acid) δ: 9.18 (s, 1H), 8.31 (dd, 1H, J = 12.5 Hz, 2.5 Hz), 7.60 (brs, 2H), 7.50 (d, 2H, J = 12 Hz), 7.26 (d, 2H, J = 12 Hz).

EXAMPLE 7

To a solution of 6,8-Difluoro-1-(4-hydroxyphenyl)-7-(1-piperazinyl)-1,4-dihydro-4-oxoquinoline-3-carboxylic acid (4.18 g) in DMF (29 ml) is added a solution of methyl iodide (7.7 g) in DMF (20 ml). The mixture is heated in a stainless steel autoclave on an oil bath at 110°–120° C. for 5 hours. DMF is distilled off under reduced pressure, and to the residue is added 10% aqueous sodium hydroxide to regulate pH 13. The insoluble substance is filtered off, and the remaining mixture is regulated to pH 8 with acetic acid. The precipitated crystals are separated by filtration, washed with water, dried, and then recrystallized from DMF to give 6,8-difluoro-1-(4-hydroxyphenyl)-7-(4-methyl-1-piperazinyl)-1,4-dihydro-4-oxoquinoline-3-carboxylic acid (1.7 g) as pale yellowish white crystals, m.p. >300° C.

Elementary analysis for $C_{21}H_{19}N_3O_4F_2$: Calcd. (%): C, 60.72; H, 4.61; N, 10.12. Found (%): C, 60.66; H, 4.70, N, 10.18.

NMR (trifluoroacetic acid) δ: 9.18 (s, 1H), 8.30 (dd, 1H, J=12 Hz, 2.5 Hz), 7.51 (d, 2H, J=9 Hz), 7.25 (d, 2H, J=9 Hz), 3.27 (m, 8H), 3.15 (d, 3H, J=5 Hz).

In the same manner as described above by using an appropriate stating material, the same compounds as obtained in Examples 4 and 6 are obtained.

EXAMPLE 8

6,8-Difluoro-1-(4-hydroxyphenyl)-7-(1-piperazinyl)-1,4-dihydro-4-oxoquinoline-3-carboxylic acid (0.80 g) is added slowly to a mixture of 90% formic acid (4 ml) and 37% formaline (4 ml) under ice-cooling. After the addition, the mixture is refluxed for 5 hours. The reaction mixture is distilled to dryness under reduced pressure. The residue is suspended in saturated aqueous sodium hydrogen carbonate (15 ml), and the mixture is stirred at room temperature for 30 minutes. The precipitated crystals are separated by filtration, washed with water, dried, and then recrystallized from DMF to give 6,8-difluoro-1-(4-hydroxyphenyl)-7-(4-methyl-1-piperazinyl)-1,4-dihydro-4-oxoquinoline-3-carboxylic acid (0.52 g) as pale yellowish white crystals, m.p. 300° C.

NMR (trifluroacetic acid) $\delta$: 9.18 (s, 1H), 8.30 (dd, 1H, J=12 Hz, 2.5 Hz), 7.51 (d, 2H, J=9 Hz), 7.25 (d, 2H, J=9 Hz), 3.27 (m, 8H), 3.15 (d, 3H, J=5 Hz).

In the same manner as described above by using an appropriate starting material, there are obtained the same compounds as obtained in Examples 4 and 6.

EXAMPLE 9

6,8-Difluoro-7-(4-methyl-1-piperazinyl)-1-(4-hydroxyphenyl)-1,4-dihydro-4-oxoquinoline-3-carboxylic acid (0.14 g) is dissolved in dry pyridine (5 ml) and acetic anhydride (5 ml), and the mixture is allowed to stand at room temperature for 16 hours. Excess acetic anhydride and pyridine are distilled off under reduced pressure, and the resulting residue is dissolved in dichloromethane. The dichloromethane solution is washed with diluted hydrochloric acid, saturated aqueous sodium chloride, saturated aqueous sodium hydrogen carbonate and saturated aqueous sodium chloride in this order, and dried over sodium sulfate. The solvent is distilled off, and the residue is recrystallized from ethanol-chloroform to give 6,8-difluoro-7-(4-methyl-1-piperazinyl)-1-(4-acetyloxyphenyl)-1,4-dihydro-4-oxoquinoline-3-carboxylic acid (0.12 g) as pale yellowish white crystals, m.p. 247°–251° C.

Elementary analysis for $C_{23}H_{21}N_3O_5F_2$: Calcd. (%): C, 60.39; H, 4.63; N, 9.19. Found (%): C, 60.32; H, 4.67, N, 9.23.

In the same manner as described above by using an appropriate starting material, there is obtained the following compound.

6,8-Difluoro-1-(2-fluoro-4-acetyloxyphenyl)-7-(4-methyl-1-piperazinyl)-1,4-dihydro-4-oxoquinoline-3-carboxylic acid, pale yellowish white crystals, m.p. 224°–225.5° C. (dec.) (recrystallized from ethanol)

PREPARATION 1

An injection preparation is prepared from the following components.

| Components | Amount |
| --- | --- |
| 6,8-Difluoro-1-(4-hydroxyphenyl)-7-(1-piperazinyl)-1,4-dihydro-4-oxoquinoline-3-carboxylic acid | 200 mg |
| Glucose | 250 mg |
| Distilled water for injection | q.s. |
| Totally | 5 ml |

6,8-Difluoro-1-(4-hydroxyphenyl)-7-(1-piperazinyl)-1,4-dihydro-4-oxoquinoline-3-carboxylic acid and glucose are dissolved in distilled water for injection, and the solution is added to a 5 ml ampoule, which is purged with nitrogen gas and then subjected to sterilization at 121° C. for 15 minutes to give an injection preparation.

PREPARATION 2

Film coated tablets are prepared from the following components.

| Components | Amount |
| --- | --- |
| 6,8-Difluoro-1-(4-hydroxyphenyl)-7-(4-methyl-1-piperazinyl)-1,4-dihydro-4-oxoquinoline-3-carboxylic acid | 100 g |
| Avicel (tradename of microcrystalline cellulose, manufactured by Asahi Chemical, Japan) | 40 g |
| Corn starch | 30 g |
| Magnesium stearate | 2 g |
| TC-5 (tradename of hydroxypropyl methylcellulose, manufactured by Shinetsu Kagaku Kogyo, Japan) | 10 g |
| Polyethylene glycol 6000 | 3 g |
| Castor oil | 40 g |
| Ethanol | 40 g |

6,8-Difluoro-1-(4-hydroxyphenyl)-7-(4-methyl-1-piperazinyl)-1,4-dihydro-4-oxoquinoline-3-carboxylic acid, Avicel, corn starch and magnesium stearate are mixed and kneaded and the mixture is tabletted using a conventional pounder (R 10 mm) for sugar coating (manufactured by Kikusui Seisakusho Co., Ltd., Japan). The tablets thus obtained are coated with a film coating agent consisting of TC-5, polyethylene glycol 6000, castor oil and ethanol to give film coated tablets.

PREPARATION 3

An oinment is prepared from the following components.

| Components | Amount |
| --- | --- |
| 6,8-Difluoro-1-(4-hydroxyphenyl)-7-(1-piperazinyl)-1,4-dihydro-4-oxoquinoline-3-carboxylic acid | 2 g |
| Purified lanolin | 5 g |
| Bleached beeswax | 5 g |
| White vaseline | 88 g |
| Totally | 100 g |

Bleached beeswax is made liquid by heating, and thereto are added 6,8-difluoro-1-(4-hydroxyphenyl)-7-(1-piperazinyl)-1,4-dihydro-4-oxoquinoline-3-carboxylic acid, purified lanolin and while vaseline, and the mixture is heated until it becomes liquid. The mixture is stirred until it is solidified to give an ointment.

PREPARATION 4

An injection preparation is prepared from the following components.

| Components | Amount |
| --- | --- |
| 6,8-Difluoro-1-(4-hydroxyphenyl)-7-(4-methyl-1-piperazinyl)-1,4-dihydro-4-oxoquinoline-3-carboxylic acid | 200 mg |

-continued

| Components | Amount |
|---|---|
| Glucose | 250 mg |
| Distilled water for injection | q.s. |
| Totally | 5 ml |

6,8-Difluoro-1-(4-hydroxyphenyl)-7-(4-methyl-1-piperazinyl)-1,4-dihydro-4-oxoquinoline-3-carboxylic acid and glucose are dissolved in distilled water for injection, and the solution is added to a 5 ml ampoule, which is purged with nitrogen gas and then subjected to sterilization at 121° C. for 15 minutes to give an injection preparation.

PREPARATION 5

Film coated tablets are prepared from the following components.

| Components | Amount |
|---|---|
| 6,8-Difluoro-1-(4-hydroxy-2-fluorophenyl)-7-(1-piperazinyl)-1,4-dihydro-4-oxoquinoline-3-carboxylic acid | 100 g |
| Avicel (tradename of microcrystalline cellulose, manufactured by Asahi Chemical, Japan) | 40 g |
| Corn starch | 30 g |
| Magnesium stearate | 2 g |
| TC-5 (tradename of hydroxypropyl methylcellulose, manufactured by Shinetsu Kagaku Kogyo, Japan) | 10 g |
| Polyethylene glycol 6000 | 3 g |
| Castor oil | 40 g |
| Ethanol | 40 g |

6,8-Difluoro-1-(4-hydroxyphenyl)-7-(1-piperazinyl)-1,4-dihydro-4-oxoquinoline-3-carboxylic acid, Avicel, corn starch and magnesium stearate are mixed and kneaded and the mixture is tabletted using a conventional pounder (R 10 mm) for sugar coating (manufactured by Kikusui Seisakusho Co., Ltd., Japan). The tablets thus obtained are coated with a film coating agent consisting of TC-5, polyethylene glycol 6000, castor oil and ethanol to give film coated tablets.

EXPERIMENT 1

(Antimicrobial activity in in vitro)

The antimicrobial activity of the test compounds as mentioned below was tested by measuring minimum inhibitory concentration (MIC) by the serial dilution method on agar plate [cf. Chemotherapy, 22, 1126–1128 (1974)]. The microorganisms were used in a concentration of $1 \times 10^8$ cells/ml (O.D. 660 m$\mu$, 0.07–0.16) and $1 \times 10^6$ cells/ml (100 folds dilution). The results are shown in Table 1. [Test compound]:

1. 6,8-Difluoro-1-(4-hydroxyphenyl)-7-(4-methyl-1-piperazinyl)-1,4-dihydro-4-oxoquinoline-3-carboxylic acid
2. 6,8-Difluoro-1-(4-fluorophenyl)-7-(1-piperazinyl)-1,4-dihydro-4-oxoquinoline-3-carboxylic acid
3. 6,8-Difluoro-1-(4-acetyloxyphenyl)-7-(4-methyl-1-piperazinyl)-1,4-dihydro-4-oxoquinoline-3-carboxylic acid
4. 6,8-Difluoro-1-(2-fluoro-4-hydroxyphenyl)-7-(4-methyl-1-piperazinyl)-1,4-dihydro-4-oxoquinoline-3-carboxylic acid
5. 6,8-Difluoro-1-(2-fluoro-4-acetyloxyphenyl)-7-(4-methyl-1-piperazinyl)-1,4-dihydro-4-oxoquinoline-3-carboxylic acid A. 6-Fluoro-1-(4-fluorophenyl)-7-(4-methyl-1-piperazinyl)-1,4-dihydro-4-oxoquinoline-3-carboxylic acid (Reference compound, disclosed in Abstracts of The 1984 ICAAC, page 102)

B. 6-Fluoro-1-(4-fluorophenyl)-7-(1-piperazinyl)-1,4-dihydro-4-oxoquinoline-3-carboxylic acid (Reference compound, disclosed in Abstracts of the 1984 ICAAC, page 102)

C. 6-Fluoro-1-(4-hydroxyphenyl)-7-(4-methyl-1-piperazinyl)-1,4-dihydro-4-oxoquinoline-3-carboxylic acid (Reference compound, disclosed in European Patent Publication No. 0131839)

TABLE 1

| Test microorganisms | Test Compd. No. 1 | | Test Compd. No. 2 | | Test Compd. No. 3 | | Test Compd. No. 4 | |
|---|---|---|---|---|---|---|---|---|
| | $1 \times 10^8$ | $1 \times 10^6$ | $1 \times 10^8$ | $1 \times 10^6$ | $1 \times 10^8$ | $1 \times 10^6$ | $1 \times 10^8$ | $1 \times 10^6$ |
| Staphylococcus aureus FDA 209P | <0.048 | <0.048 | 0.39 | 0.195 | 0.195 | 0.195 | 0.195 | 0.097 |
| Staphylococcus pyrogens IID S-23 | 0.781 | 0.39 | 12.5 | 6.25 | 6.25 | 3.12 | 1.56 | 1.56 |
| Escherichia coli NIHJ JC-2 | <0.048 | <0.048 | <0.048 | <0.048 | <0.048 | <0.048 | 0.097 | 0.097 |
| Escherichia coli No. 29 | <0.048 | <0.048 | <0.048 | <0.048 | <0.048 | <0.048 | 0.195 | 0.097 |
| Klebsiella pneumoniae NCTC 9632 | <0.048 | <0.048 | <0.048 | <0.048 | 0.195 | 0.097 | 0.195 | 0.195 |
| Proteus inconstans IFO 12930 | 0.195 | 0.097 | 0.39 | 0.195 | 3.12 | 1.56 | 3.12 | 1.56 |
| Proteus morganii IID Kono | 0.097 | <0.048 | 0.097 | 0.048 | 1.56 | 0.781 | 1.56 | 0.781 |
| Serratia marcescens IFO 12648 | <0.048 | <0.048 | 0.195 | 0.097 | 0.781 | 0.39 | 0.781 | 0.781 |
| Acinetobacter calcoaceticus AC-54 | 0.097 | <0.048 | 0.39 | 0.195 | 1.56 | 0.781 | 0.781 | 0.781 |
| Pseudomonas aeruginosa ATCC 10145 | 0.39 | 0.195 | 1.56 | 0.781 | 1.56 | 1.56 | 3.12 | 1.56 |
| Pseudomonas aeruginosa E-2 | 0.195 | 0.097 | 1.56 | 0.781 | 1.56 | 1.56 | 3.12 | 1.56 |
| Bacillus subtilis ATCC 6633 | <0.048 | <0.048 | 0.195 | 0.097 | 0.195 | 0.097 | 0.39 | 0.195 |
| Streptococcus faecalis IFO 12580 | 0.195 | 0.097 | 6.25 | 3.12 | 1.56 | 0.781 | 0.781 | 0.781 |

| Test microorganisms | Test Compd. No. 5 | | Test Compd. A | | Test Compd. B | | Test Compd. C | |
|---|---|---|---|---|---|---|---|---|
| | $1 \times 10^8$ | $1 \times 10^6$ | $1 \times 10^8$ | $1 \times 10^6$ | $1 \times 10^8$ | $1 \times 10^6$ | $1 \times 10^8$ | $1 \times 10^6$ |
| Staphylococcus aureus FDA 209P | 0.097 | 0.097 | 0.39 | 0.195 | 0.39 | 0.195 | 0.097 | <0.048 |
| Staphylococcus pyrogens IID S-23 | 1.56 | 1.56 | 6.25 | 3.12 | 6.25 | 3.12 | 1.56 | 0.78 |
| Escherichia coli NIHJ JC-2 | 0.097 | <0.048 | 0.195 | 0.195 | 0.097 | <0.048 | 0.097 | 0.097 |
| Escherichia coli No. 29 | 0.097 | <0.048 | 0.195 | 0.097 | 0.097 | <0.048 | 0.097 | <0.048 |
| Klebsiella pneumoniae NCTC 9632 | 0.097 | 0.097 | 0.195 | 0.195 | 0.097 | <0.048 | 0.097 | <0.048 |
| Proteus inconstans IFO 12930 | 3.12 | 1.56 | 3.12 | 3.12 | 0.78 | 0.78 | 0.78 | 0.39 |
| Proteus morganii IID Kono | 1.56 | 0.781 | 0.78 | 0.78 | 0.195 | 0.195 | 0.39 | 0.39 |
| Serratia marcescens IFO 12648 | 0.781 | 0.781 | 3.12 | 0.78 | 0.39 | 0.195 | 0.39 | 0.195 |
| Acinetobacter calcoaceticus AC-54 | 0.781 | 0.39 | 0.39 | 0.39 | 0.39 | 0.195 | 0.39 | 0.195 |
| Pseudomonas aeruginosa ATCC 10145 | 3.12 | 1.56 | 3.12 | 3.12 | 1.56 | 0.78 | 1.56 | 0.78 |
| Pseudomonas aeruginosa E-2 | 1.56 | 1.56 | 3.12 | 3.12 | 0.78 | 0.78 | 0.78 | 0.39 |
| Bacillus subtilis ATCC 6633 | 0.39 | 0.195 | 0.195 | 0.097 | 0.195 | 0.097 | 0.097 | 0.097 |

TABLE 1-continued

| | | | | | | | |
|---|---|---|---|---|---|---|---|
| Streptococcus faecalis IFO 12580 | 1.56 | 0.781 | — | — | — | — | — |

EXPERIMENT 2

(Absorption by oral admonistration in monkey)

The test compounds were dissolved in 0.1N hydrochloric acid or suspended in 0.5% sodium carboxymethyl cellulose solution. The solution or suspension was administered into stomach of monkey (two monkeys) with cathetel. After the administration of test compounds, the blood was collected from the lower limbs vein at a fixed interval with a syringe treated with heparin. The collected blood was centrifuged at 3,000 r.p.m. for 10 minutes to separate the plasma. The concentration of the test compound was measured by a thin layer cup method (a bio-assay), wherein *Bacillus subtilis* ATCC 6633 was used as a bacteria for determination. Based on a standard curve, the concentration of test compound in plasma was calculated. The results are shown in Table 2.

TABLE 2

| Test compd. No. | Dose (mg/kg) | Run No. | Amount of test compd. in plasma ($\gamma$/ml) Time (hour) | | | | | |
|---|---|---|---|---|---|---|---|---|
| | | | 0.5 | 1 | 2 | 4 | 7 | 24 |
| 1 | 10 | 1 | 2.35 | 4.26 | 1.94 | 0.72 | N.D.[*1] | N.D.[*1] |
| | | 2 | N.D.[*1] | 2.18 | 1.12 | 1.12 | N.D.[*1] | N.D.[*1] |
| | | Average | <1.37 | 3.22 | 1.53 | 0.92 | <0.39 | <0.39 |
| C | 100 | 1 | 0.36 | 0.49 | 0.65 | 0.96 | 0.95 | 0.90 |
| | | 2 | N.D.[*2] | N.D.[*2] | N.D.[*2] | N.D.[*2] | N.D.[*2] | N.D.[*2] |
| | | Average | <0.28 | <0.35 | <0.43 | <0.58 | <0.58 | <0.55 |

[Note]:
N.D.[*1]: <0.2 $\gamma$/ml,
N.D.[*2]: <0.39 $\gamma$/ml
When the average was counted in case of N.D., it was counted as 0.2 $\gamma$/ml or 0.39 $\gamma$/ml, respectively, and the average value was shown with a head of "<" (less than)

What is claimed is:

1. A compound of the formula:

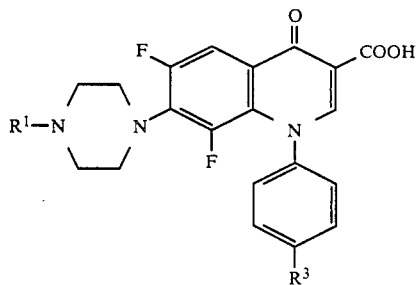

wherein $R^1$ is methyl, and $R^3$ is an alkanoyloxy having 2 to 4 carbon atoms, or a pharmaceutically acceptable salt thereof.

2. The compound according to claim 1, which is 6,8-difluoro-1-(4-acetyloxyphenyl)-7-(4-methyl-1-piperazinyl)-1,4-dihydro-4-oxoquinoline-3-carboxylic acid or a pharmaceutically acceptable salt thereof.

3. An antimicrobial composition which comprises as an essential active ingredient an effective amount of a compound of the formula:

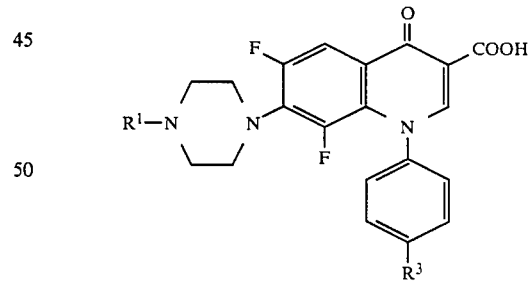

wherein $R^1$ is methyl, and $R^3$ is an alkanoyloxy having 2 to 4 carbon atoms, or a pharmaceutically acceptable salt thereof in admixture with a pharmaceutically acceptable diluent or carrier.

4. The composition according to claim 3, wherein the active compound is 6,8-difluoro-1-(4-acetyloxyphenyl)-7-(4-methyl-1-piperazinyl)-1,4-dihydro-4-oxoquinoline-3-carboxylic acid or a pharmaceutically acceptable salt thereof.

* * * * *